United States Patent
Takemura

(10) Patent No.: US 7,534,406 B2
(45) Date of Patent: May 19, 2009

(54) STEAM FOG GENERATOR FOR VEHICLE

(75) Inventor: Isao Takemura, Tokyo (JP)

(73) Assignee: S. T. Chemical Co., Ltd., Tokyo (JP)

( * ) Notice: Subject to any disclaimer, the term of this patent is extended or adjusted under 35 U.S.C. 154(b) by 759 days.

(21) Appl. No.: 10/496,432

(22) PCT Filed: Jan. 22, 2003

(86) PCT No.: PCT/JP03/00521

§ 371 (c)(1),
(2), (4) Date: Jul. 6, 2004

(87) PCT Pub. No.: WO03/066113

PCT Pub. Date: Aug. 14, 2003

(65) Prior Publication Data

US 2004/0258578 A1    Dec. 23, 2004

(30) Foreign Application Priority Data

Feb. 6, 2002    (JP)    ............................. 2002-029391

(51) Int. Cl.
| A61L 2/08 | (2006.01) |
| A62B 7/08 | (2006.01) |
| A61L 9/00 | (2006.01) |
| B01D 47/00 | (2006.01) |
| A61M 16/00 | (2006.01) |
| A61H 33/06 | (2006.01) |
| A24F 25/00 | (2006.01) |
| F25B 37/00 | (2006.01) |
| F02M 15/04 | (2006.01) |

(52) U.S. Cl. ........................... 422/305; 422/26; 422/28; 422/120; 422/124; 422/125; 261/24; 261/30; 261/102; 261/140; 261/142; 392/390; 392/391; 392/394; 239/34; 239/50; 239/57; 219/271; 219/275

(58) Field of Classification Search ................... 422/26, 422/28, 120, 124–125, 305; 261/24, 30, 261/102, 140, 142; 392/390–391, 394; 239/34, 239/50, 57; 219/271, 275
See application file for complete search history.

(56) References Cited

U.S. PATENT DOCUMENTS 4,849,606 A    7/1989    Martens, III et al.
6,090,349 A *  7/2000    Hirano ........................ 422/124

FOREIGN PATENT DOCUMENTS

| JP | 2-111277 |   | 9/1990 |
| JP | 6-247479 |   | 9/1994 |
| JP | 06247479 | * | 9/1994 |
| JP | 9-327505 |   | 12/1997 |

* cited by examiner

*Primary Examiner*—Jill Warden
*Assistant Examiner*—Monzer R Chorbaji
(74) *Attorney, Agent, or Firm*—Jordan and Hamburg LLP

(57) ABSTRACT

A stem fog generator (1) for vehicle aromatic components into a cabin and suitable for use in a vehicle, comprising a plug part (11) and a steam fog generator body (12) foldably connected to each other, wherein the plug part (11) is cylindrically formed so as to be attachable to and detachable from an accessory socket (14), a power supply from the plug part (11) is fed to a heater (71) through an operating switch (45), a loading/unloading.

20 Claims, 7 Drawing Sheets

STEAM FOG GENERATOR FOR VEHICLE

TECHNICAL FIELD

The present invention relates to a steam fog generator for vehicle capable of transpiring aromatic components into a cabin.

BACKGROUND ART

A known device capable of transpiring liquid aromatic substances into a cabin is a heating type aroma device for an automobile (see Japanese Patent Laid-Open No. 2001-327587).

The heating type aroma device for an automobile includes a plug part to be inserted into an accessory socket for supplying power to a cigarette lighter, and a knob part formed integrally with the plug part, and the knob part includes an injection hole through which liquid aromatic substances such as aroma oil are injected, and a containing part for containing the injected liquid aromatic substances. The plug part includes a heater that produces heat by the power supplied from the accessory socket, and is arranged to transpire liquid aromatic substances by heating them with the heater into the cabin, when they are injected through the injection hole.

For such a heating type aroma device for an automobile, however, the liquid aromatic substances have to be injected through the injection hole without a spill, which is cumbersome.

Vibration while driving may cause the liquid aromatic substances to spill out of the injection hole.

The invention has been achieved in view of such problems in the related art, and has an object to provide a steam fog generator for vehicle suitable for use in a vehicle.

DISCLOSURE OF THE INVENTION

In order to solve the above described problems, there is provided a steam fog generator for vehicle according to claim 1 of the invention including: a plug part attachable to and detachable from an accessory socket provided in a cabin; and a steam fog generator body extending from the plug part into the cabin, power being supplied from the vehicle through the plug part, wherein the steam fog generator body includes a holding part for attachably and detachably holding a cartridge containing liquid chemicals, a heating element that produces heat by the power supplied through the plug part to heat the liquid chemicals in a container part of the cartridge and allow the liquid chemicals to pass outward through a permeable membrane covering a top opening of the container part, and divergence means for diverging the liquid chemicals having passed through the permeable membrane into the cabin.

The liquid chemicals include aromatic substances, deodorizers, insecticide, antibacterial agents, or fungicides.

Specifically, when the steam fog generator for vehicle is used, the cartridge containing the liquid chemicals is held in the holding part of the steam fog generator body, the plug part is attached to the accessory socket in an inner surface of the cabin, and the power is supplied from the vehicle through the plug part. At this time, the heating element of the steam fog generator body produces heat by the supplied power, and heats the liquid chemicals in the container part of the cartridge. Thus, the liquid chemicals pass outward through the permeable membrane covering the top opening of the container part, and are diverged into the cabin by the divergence means of the steam fog generator body.

In the steam fog generator for vehicle according to claim 2, the steam fog generator body includes an operating switch for turning on and off the power to be supplied to the heating element.

Specifically, the supply of the power, which is supplied from the vehicle through the plug part, to the heating element is turned on and off by the operating switch provided in the steam fog generator body.

In one type of car, the accessory socket provided in the vehicle is of a type where supply of power is interrupted depending on states of a key switch of the vehicle, and in another type of car, it is of a type where power is always supplied regardless of the states of the key switch. For the latter, a heating element drains the on-vehicle battery even during parking. Even for such a type, turning off the operating switch when getting off the vehicle prevents the on-vehicle battery from being unnecessarily drained without the plug part being detached from the accessory socket.

In the steam fog generator for vehicle according to claim 3, the holding part includes a loading/unloading port for loading and unloading the cartridge into and from the steam fog generator body, and a storage space for loadably and unloadably storing the cartridge inserted through the loading/unloading port, the divergence means is constituted by a divergence port that provides communication between the storage space and the outside, at least one of the container part and the permeable membrane of the cartridge, and the steam fog generator body are made of a transparent material, and the steam fog generator body includes an observation part for observing the amount of liquid remaining in the cartridge.

Specifically, the steam fog generator body includes the loading/unloading port for loading and unloading the cartridge, and the storage space for storing the cartridge inserted through the loading/unloading port, and the cartridge inserted through the loading/unloading port is held in the storage space. At this time, the liquid chemicals transpired into the storage space are supplied into the cabin through the divergence port that is in communication with the outside.

At least one of the container part and the permeable membrane of the cartridge, and the steam fog generator body are transparent, and the steam fog generator body includes the observation part for observing the amount of liquid remaining in the cartridge held in the steam fog generator body. Thus, the amount of liquid chemicals remaining in the cartridge can be visually checked, facilitating the anticipation of when the cartridge should be replaced.

Further, in the steam fog generator for vehicle according to claim 4, the steam fog generator body extending from the plug part is foldably connected to the plug part, and limiting means is provided for limiting a folding direction of the steam fog generator body to a bottom side of the held cartridge.

Specifically, in one type of car with an accessory socket, to and from which a plug part is attached and detached, provided in a front wall surface of a driver's seat, the steam fog generator body extending from the plug part protrudes toward the driver's seat, which may be a nuisance. In this case, the steam fog generator body extending from the plug part is folded toward the plug part.

At this time, the folding direction of the steam fog generator body is limited by the limiting means to the bottom side of the held cartridge, thus preventing folding toward the front wall surface of the top opening of the cartridge. This allows the permeable membrane through which the liquid chemicals in the cartridge pass to be directed into the cabin.

BEST MODE FOR CARRYING OUT THE INVENTION

Now, the invention will be described in detail with reference to the accompanying drawings.

Figure 1:
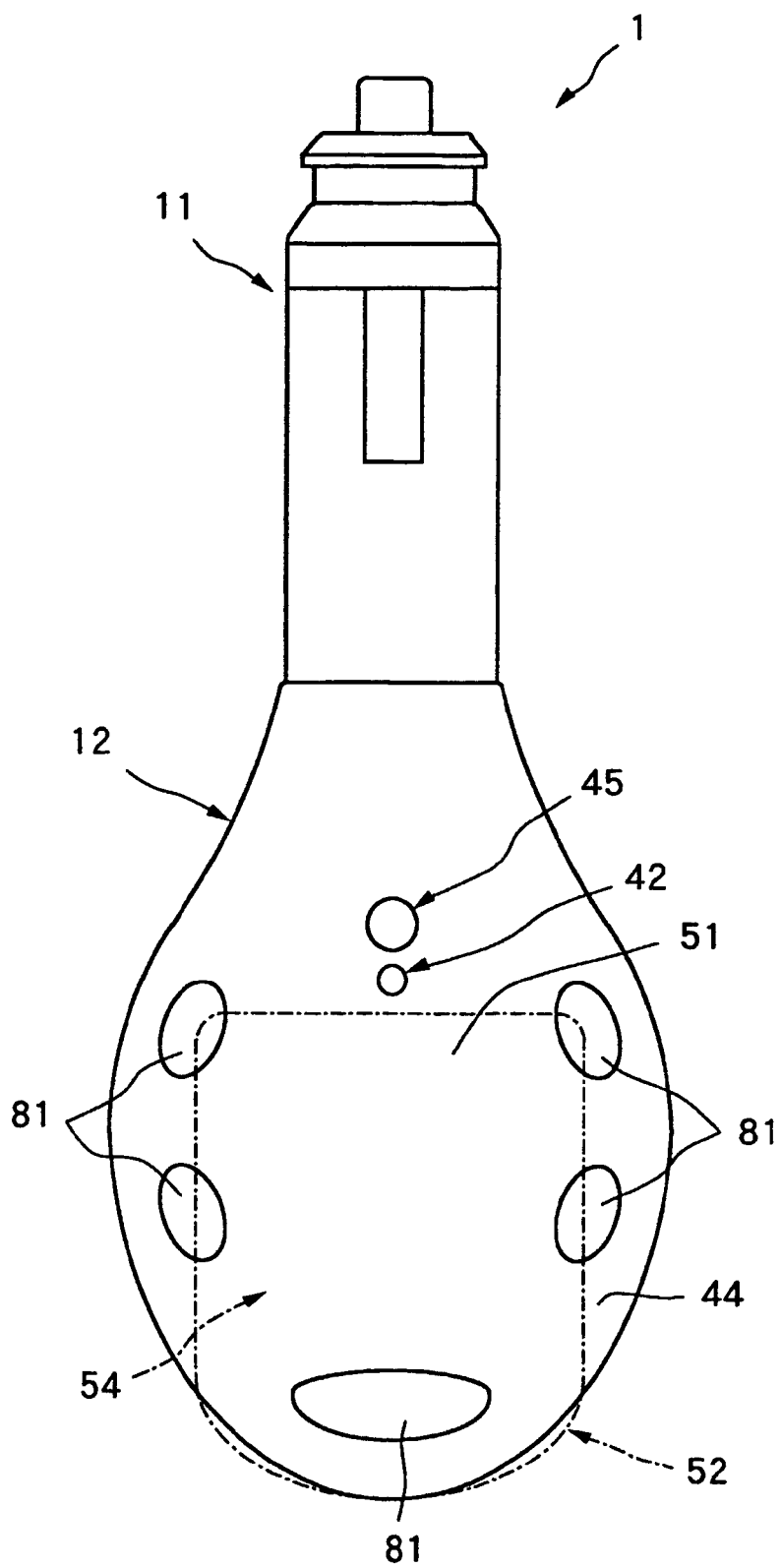
FIG. 1 is a plan view of an embodiment of the invention.

FIG. 1 shows a steam fog generator 1 for vehicle according to an embodiment, and the steam fog generator 1 for vehicle is a device capable of transpiring aromatic components into a cabin of a passenger car or the like.

Figure 2:
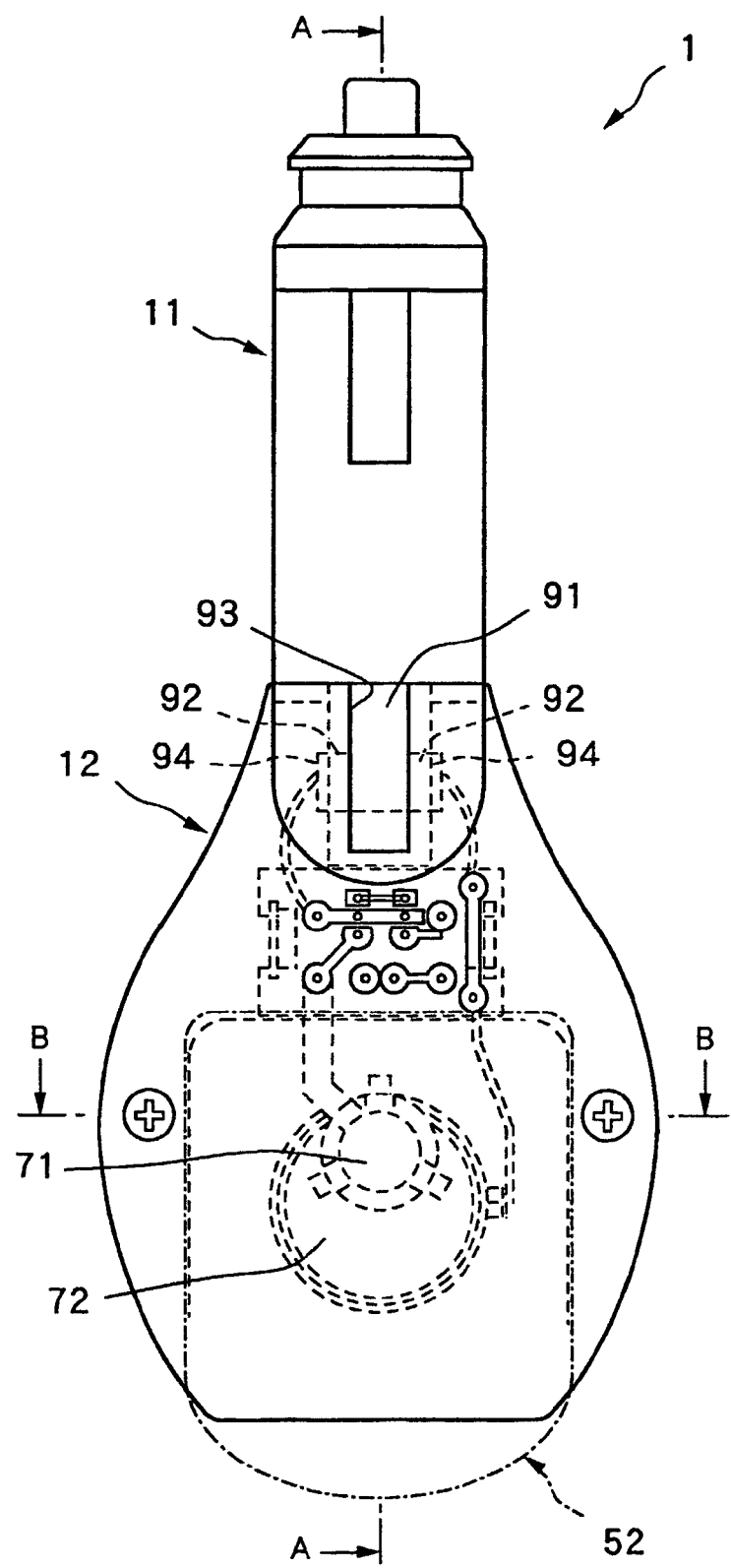
FIG. 2 is a bottom view of the embodiment.
Figure 3:
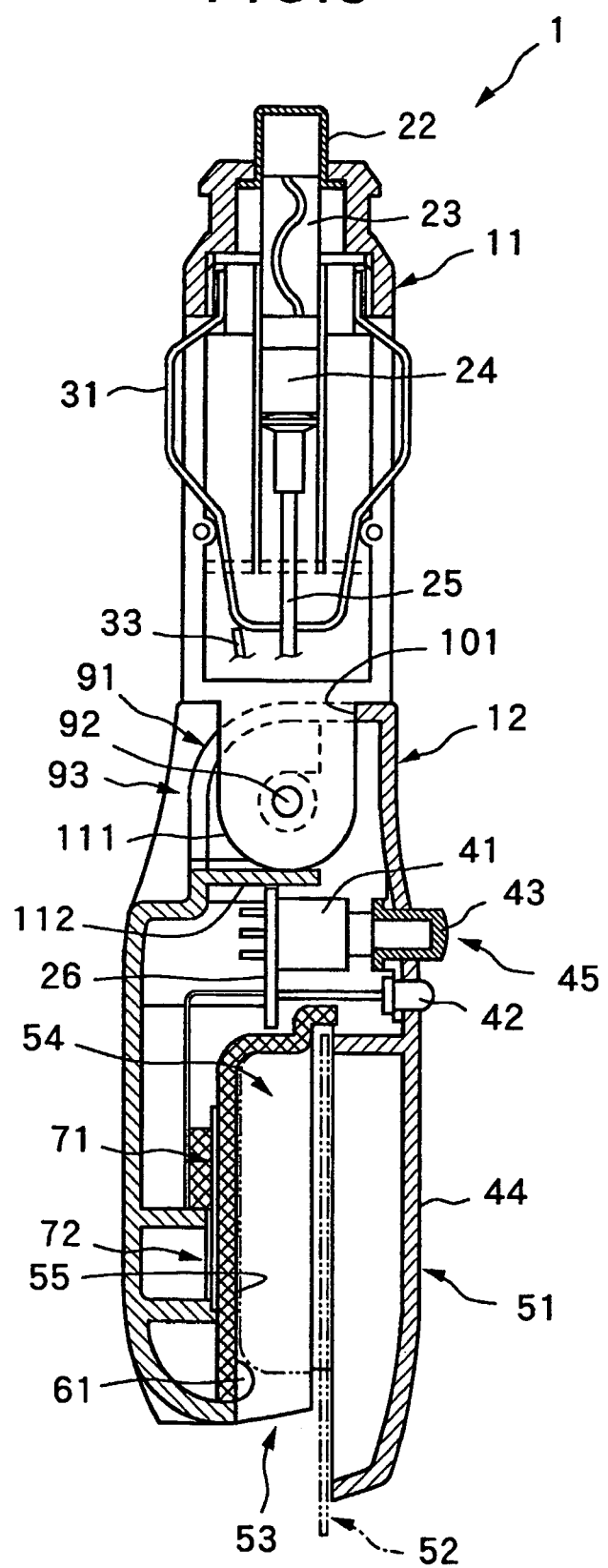
FIG. 3 is a sectional view taken along the line A-A in FIG. 2.

As shown in FIGS. 1 to 3, the steam fog generator 1 for vehicle includes a plug part 11, and an elliptical steam fog generator body 12 connected to the plug part 11. In a front part of a driver's seat in the vehicle where the steam fog generator 1 for vehicle is used, an instrument panel 13 is provided as shown in FIG. 4, and the instrument panel 13 has an accessory socket 14 for supplying power from an on-vehicle battery to a cigarette lighter or the like.

The plug part 11 is cylindrically formed so as to be attachable to and detachable from the accessory socket 14, and a positive terminal 22, which is pressed against a positive electrode 21 at an end of the accessory socket 14, protrudes from a tip of the plug part 11. As shown in FIG. 3, a fuse 23 is replaceably stored in the positive terminal 22, and an electrode 24 at the other end of the fuse 23 is connected to a substrate 26 in the steam fog generator body 12 through a harness 25 (a middle part of the harness 25 is not shown).

Figure 4:
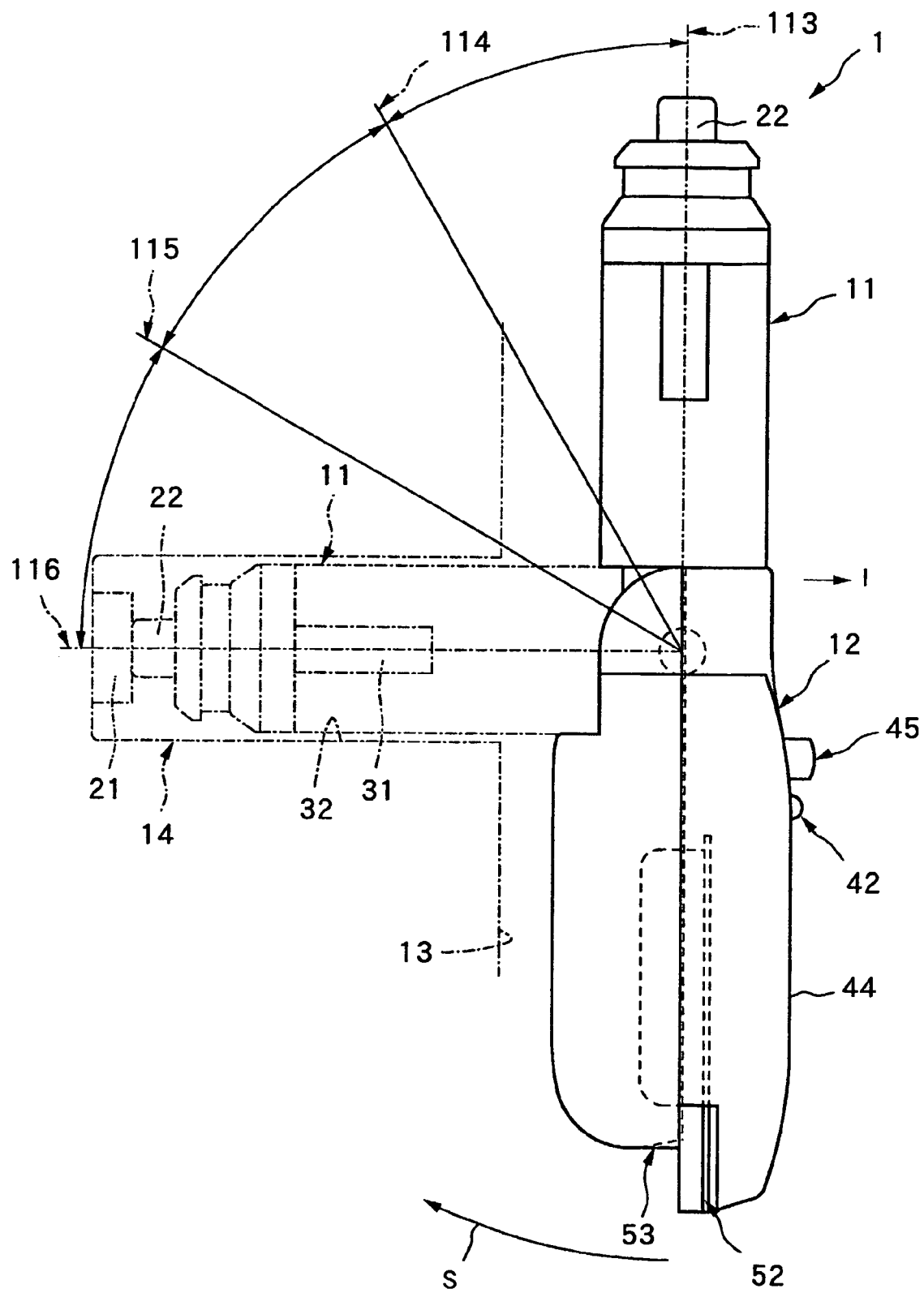
FIG. 4 is a side view of the embodiment.

An earth terminal 31 formed by folding a long metal plate is provided in the plug part 11 so as to protrude laterally, and is configured so as to be pressed against to a negative terminal 32 formed by an inner peripheral surface of the accessory socket 14 as shown in FIG. 4. As shown in FIG. 3, the earth terminal 31 is connected to the substrate 26 through the harness 33 (a middle part of the harness 33 is not shown), and the power from the on-vehicle battery is supplied to the substrate 26 through the accessory socket 14.

On the substrate 26 to which the power is supplied, a push bottom switch 41 and a light emitting diode 42 are provided, and a button 43 of the switch 41 and the light emitting diode 42 protrude from an upper surface 44 of the steam fog generator body 12. In the steam fog generator body 12, the switch 41 and the button 43 constitute an operating switch 45 for turning on and off the power, the power is alternately turned on and off for each push of the button 43 of the operating switch 45, and when the power is on, the light emitting diode 42 is lit.

The steam fog generator body 12 is provided so as to extend into the cabin I from the plug part 11 inserted into the accessory socket 14. The steam fog generator body 12 is made of colorless and transparent plastic, and as shown in FIG. 1, an entire surface thereof constitutes an observation part 51 through which the inside can be seen. As shown in FIG. 3, a loading/unloading port 53 for loading and unloading a cartridge 52 into and from the steam fog generator body 12 is provided at an end of the steam fog generator body 12, and a storage space 54 for loadably and unloadably storing the cartridge 52 inserted through the loading/unloading port 53 is formed inside the loading/unloading port 53. The storage space 54 is formed between a support surface 55 that supports the cartridge 52 from the bottom and the upper surface 44 of the steam fog generator body 12, and constitutes a holding part of the invention.

Figure 5:
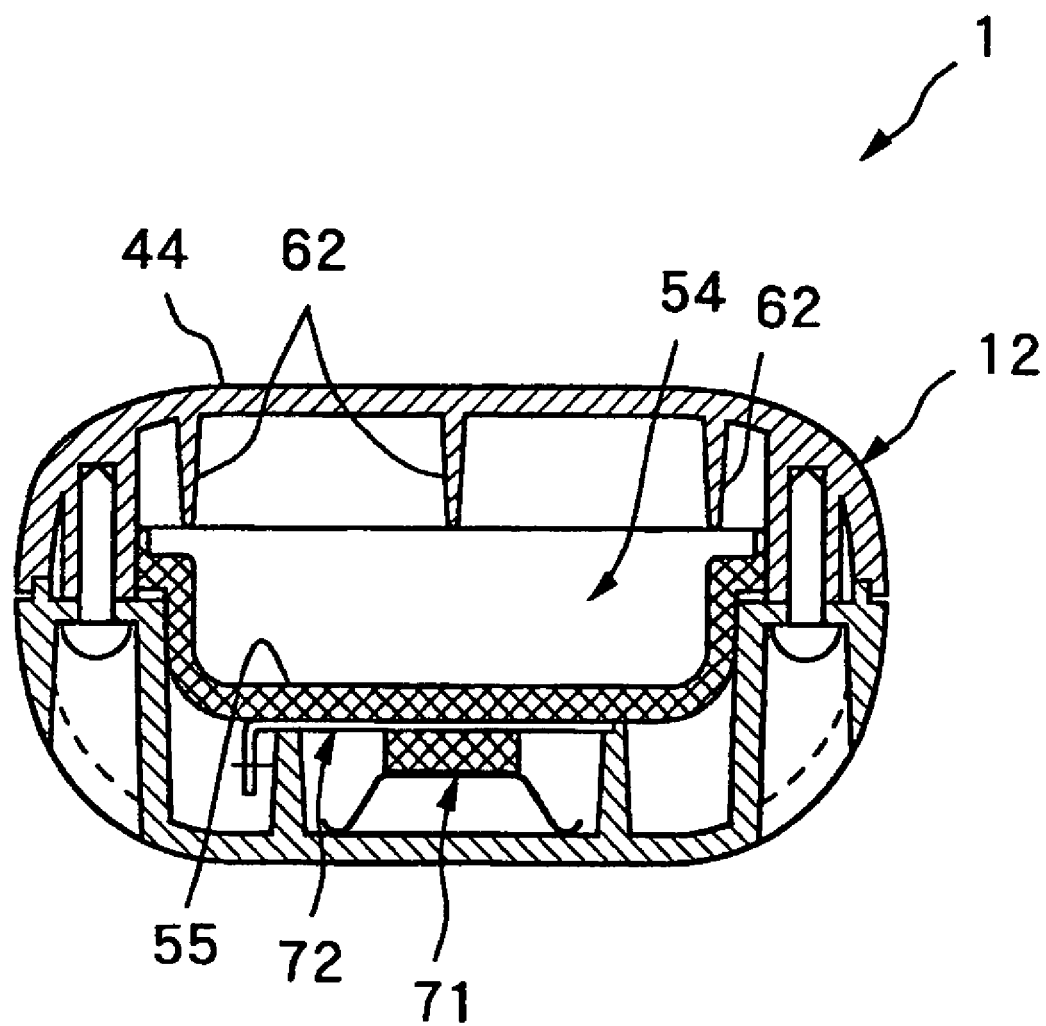
FIG. 5 is a sectional view taken along the line B-B in FIG. 2.

A protruding part 61 protrudes from the support surface 55, which prevents the cartridge 52 stored in the storage space 54 from being removed out of the loading/unloading port 53, and three ribs 62, . . . that support the top of the cartridge 52 are integrally formed in the steam fog generator body 12 as shown in FIG. 5.

As shown in FIGS. 2, 3, and 5, a cylindrical heater 71 as a heating element is provided on a back surface of the support surface 55, and power is supplied to the heater 71 via the switch 41. Between the heater 71 and the support surface 55, a metal plate 72 in the shape of a disk with a large diameter is provided in intimate contact with the support surface 55, and the heat from the heater 71 can be extensively transferred.

As shown in FIG. 1, a plurality of divergence ports 81, . . . are provided in the upper surface 44 of the steam fog generator body 12, and the divergence ports 81, . . . constitute divergence means of the invention that provides communication between the storage space 54 and the outside. Thus, the cartridge 52 stored in the storage space 54 can be heated by the heater 71, and when liquid chemicals in the cartridge 52 are transpired, the liquid chemicals can be diverged from the divergence ports 81, . . . into the cabin I.

As shown in FIGS. 2 and 3, a thick connecting part 91 extends from a rear end of the plug part 11, and cylindrical connecting shafts 92, 92 protrude from both sides of the connecting part 91. As shown in FIG. 2, the connecting shafts 92, 92 are rotatably supported in circular holes 94, 94 in both sides of a notch groove 93 with the connecting part 91 being inserted into the notch groove 93 of the steam fog generator body 12, and the steam fog generator body 12 extending from the plug part 11 is foldably connected to the plug part 11 as shown in FIG. 4.

As shown in FIG. 3, the notch groove 93 is closed on the side of the upper surface 44 of the steam fog generator body 12, and a stopper 101 as limiting means that protrudes toward and abuts against the connecting part 91 is formed at the end of the upper surface 44. Thus, using a state where the plug part 11 and the steam fog generator body 12 are placed in line as the reference, a folding direction S of the steam fog generator body 12 with respect to the plug part 11 is limited to the direction of the arrow in FIG. 4, and is set on the bottom side of the cartridge 52 held in the storage space 54.

As shown in FIG. 3, the end of the connecting part 91 is formed into an arc, and a plurality of detents (not shown) protrude from the arcuate surface 111 at intervals in a rotational direction around the connecting shaft 92. The detents are set to a height such as to abut against an end surface 112 that forms one wall surface of the notch groove 93, and configured, as shown in FIG. 4, so as to maintain a first state 113 where the connecting part 91 and the steam fog generator body 12 are placed in line, a second state 114 where they are folded 30 degrees, a third state 115 where they are folded 60 degrees, and a fourth state 116 where they are folded 90 degrees.

Figure 6:
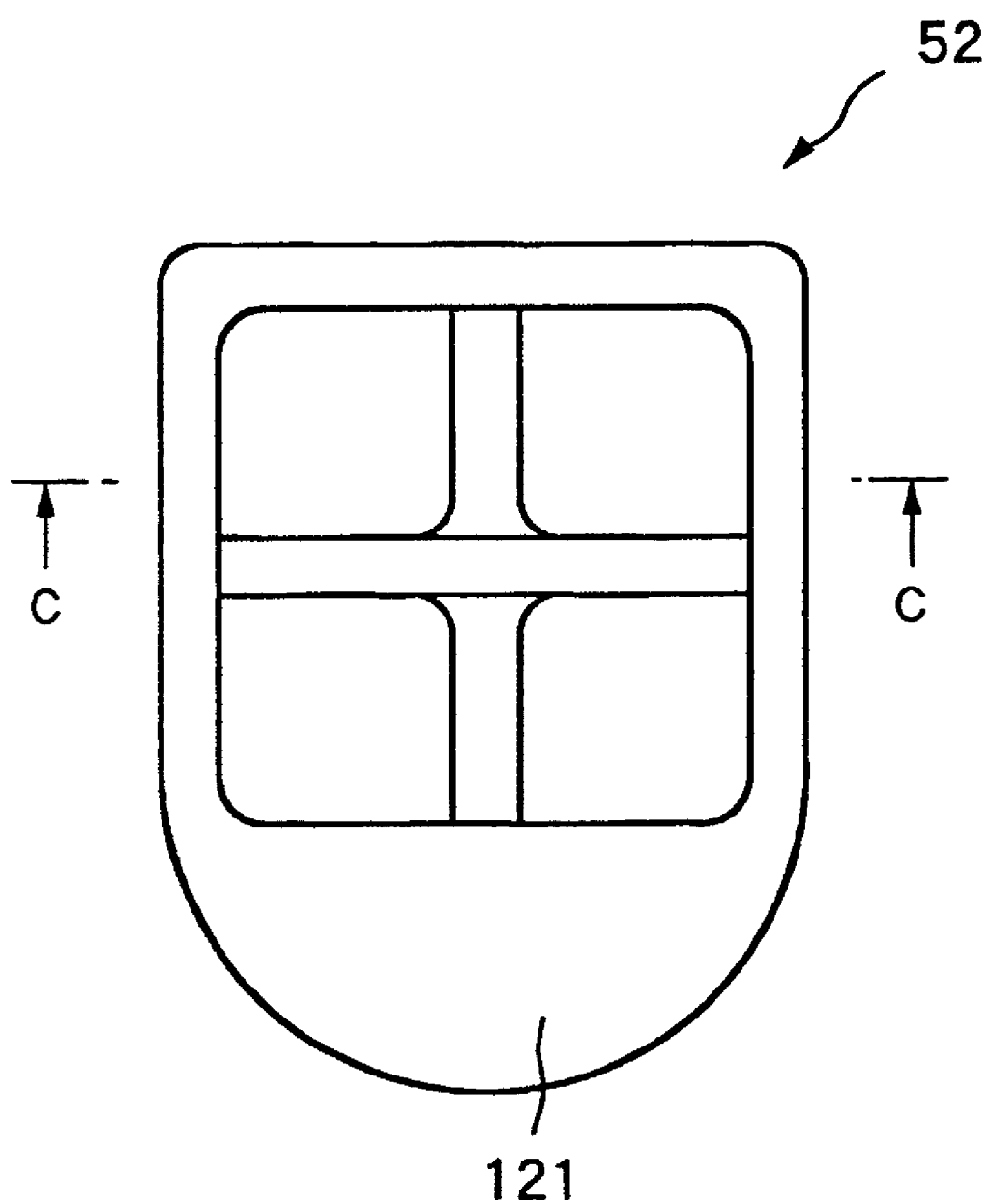
FIG. 6 is a plan view of a cartridge of the embodiment.
Figure 7:
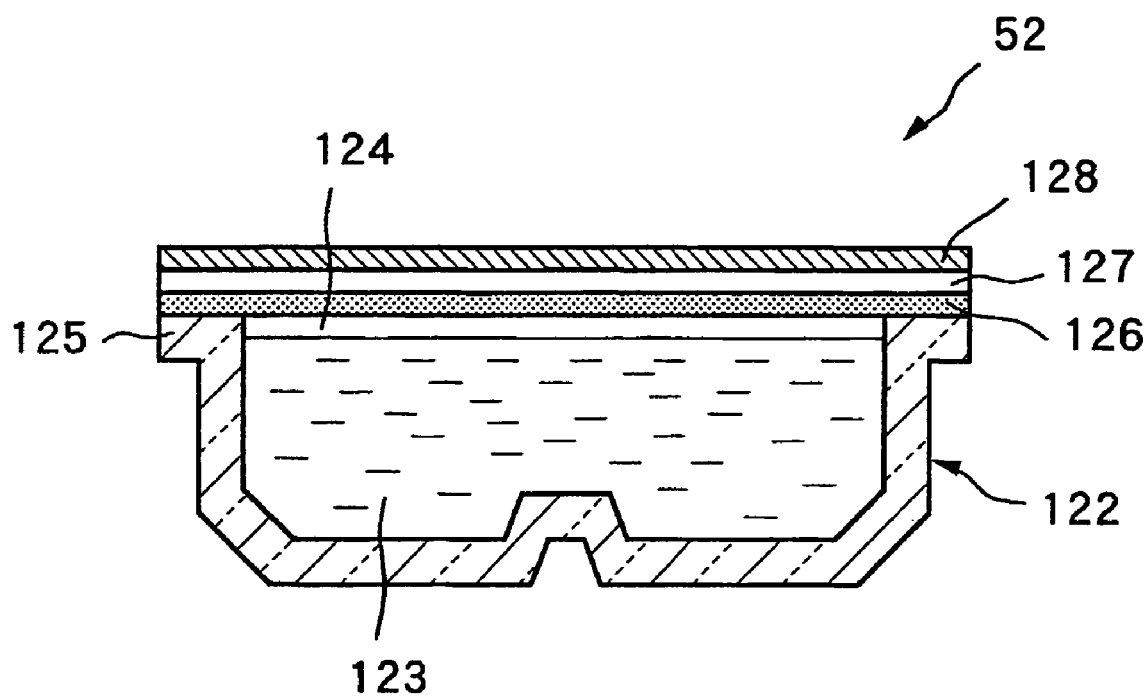
FIG. 7 is a sectional view taken along the line C-C in FIG. 6.

On the other hand, as shown in FIG. 6, the cartridge 52 is formed into a rectangle, and has an arcuate tongue 121 at an end thereof. The cartridge 52 includes a colorless and transparent container part 122 as shown in FIG. 7, and the container part 122 contains colored liquid chemicals 123 containing chemicals such as aromatic components, deodorizing components, insecticidal components, antibacterial components, or fungicidal components. A flange 125 extending laterally is formed on an opening edge of a top opening 124 of the container part 122, a colorless and transparent permeable membrane 127 is bonded to the flange 125 via a colorless and transparent seal layer 126, and the permeable membrane 127 closes the top opening 124. Thus, the amount of liquid remaining in the colorless and transparent cartridge 52 can be observed from the outside of the colorless and transparent steam fog generator body 12.

The permeable membrane 127 is constituted by a membrane that prevents an escape of the liquid chemicals 123 at normal times, but allows the liquid chemicals 123 heated by the heater 71 and transpired to permeate therethrough. Thus, heating the cartridge 52 by the heater 71 allows the liquid chemicals 123 to pass out of the cartridge 52, and allows the liquid chemicals 123 having passed through the permeable membrane 127 to be diverged into the cabin I through the divergence ports 81, . . . . The entire permeable membrane 127 is removably covered with an aluminum seal 128 at the point of sale.

According to the embodiment including the above described configurations, when the steam fog generator 1 for vehicle is used, the cartridge 52 with the aluminum seal 128 being removed is stored in the storage space 54 through the loading/unloading port 53 in the steam fog generator body 12. In this state, the plug part 11 is inserted into the accessory socket 14 provided in the instrument panel 13, and the power is supplied from the on-vehicle battery.

Then, the operating switch 45 of the steam fog generator body 12 is turned on to energize the heater 71, and the liquid chemicals 123 in the cartridge 52 are heated by the heater 71 that produces heat from the bottom of the container part 122. Thus, the liquid chemicals 123 can be transpired through the permeable membrane 127 covering the top opening 124 of the container part 122 into the storage space 54, and supplied into the cabin I through the divergence ports 81, . . . that communicate with the outside.

Thus, simply setting the cartridge 52 containing the liquid chemicals 123 in the steam fog generator body 12, and attaching the plug part 11 to the accessory socket 14 allow the liquid chemicals 123 in the cartridge 52 to be transpired into the cabin I.

This saves trouble of injecting liquid aromatic substances through an injection hole without a spill, and improves convenience. Because the cartridge 52 is attachably and detachably held, favorite aromatic agents or deodorizers can be obtained simply by replacing the cartridge 52 with a cartridge 52 containing different liquid chemicals. This improves usability as compared with a conventional device that does not allow replacement of liquid aromatic substances until injected substances run out.

Then, the liquid chemicals 123 are contained in the container part 122 of the cartridge 52, and the top opening 124 of the container part 122 is covered with the permeable membrane 127. Thus, vibration while driving causes no spill of the liquid chemicals 123, and the steam fog generator 1 for vehicle is more suitable for use in vehicles than a conventional device that may cause a spill of liquid aromatic substances through an injection hole.

The steam fog generator body 12 has the operating switch 45 for energizing and de-energizing the heater 71, and operating the operating switch 45 allows the heater 71 to be turned on and off. Thus, turning on and off the operating switch 45 allows the amount of transpired liquid chemicals 123 to be adjusted.

The accessory socket 14 provided in the vehicle is of a type where supply of power is interrupted depending on states of a key switch of the vehicle, or a type where power is always supplied regardless of the states of the key switch. For the latter, the heater 71 drains the on-vehicle battery even during parking. Even for such a type, turning off the operating switch 45 when getting off the vehicle prevents the on-vehicle battery from being unnecessarily drained without the plug part 11 being detached from the accessory socket 14.

The container part 122 and the permeable membrane 127 of the cartridge 52 and the steam fog generator body 12 are colorless and transparent, and the entire surface of the steam fog generator body 12 constitutes the observation part 51 through which the amount of liquid remaining in the cartridge 52 in the steam fog generator body 12 can be observed. Thus, the amount of liquid chemicals 123 remaining in the cartridge 52 can be visually checked from the outside, and the replacement timing of the cartridge 52 can be anticipated to provide for running out of the liquid chemicals 123.

Further, the plug part 11 and the steam fog generator body 12 are foldably connected via the connecting shaft 92, and the stopper 101 of the steam fog generator body 12 abuts against the connecting part 91 of the plug part 11. Thus, the folding direction S of the steam fog generator body 12 is set on the bottom side of the cartridge 52 held therein as shown in FIG. 4, using the state where the plug part 11 and the steam fog generator body 12 are placed in line as the reference.

Thus, with the plug part 11 being attached to the accessory socket 14 provided in the instrument panel 13 in the front part of the driver's seat, the steam fog generator body 12 that protrudes toward the driver's seat and is a nuisance can be folded. In FIG. 4, a state of folding downward is shown, but rotating the cylindrical plug part 11 allows folding laterally or upward.

Thus, the protruding direction into the cabin I can be changed, which allows accommodation depending on usage patterns and improves convenience.

Because the folding direction S of the steam fog generator body 12 is limited to the bottom side of the cartridge 52 held therein, folding of the top opening 124 of the cartridge 52 toward the instrument panel 13 can be prevented, and the permeable membrane 127 through which the liquid chemicals 123 in the cartridge 52 pass, and the divergence ports 81, . . . through which the liquid chemicals 123 having passed through the permeable membrane 127 are supplied can be directed into the cabin I. This allows the transpired liquid chemicals 123 to be diverged into the cabin I.

INDUSTRIAL APPLICABILITY

As described above, in the steam fog generator for vehicle according to claim 1 of the invention, simply holding the cartridge containing the liquid chemicals such as aromatic components in the holding part of the steam fog generator body, and attaching the plug part to the accessory socket in an inner surface of the cabin allow the liquid chemicals in the cartridge to be transpired into the cabin.

This saves trouble of injecting liquid aromatic substances through an injection hole without a spill, and improves convenience. Because the cartridge is attachably and detachably held, favorite aromatic agents or deodorizers can be obtained simply by replacing the cartridge with a cartridge containing different liquid chemicals. This improves usability as compared with a conventional device that does not allow replacement of liquid aromatic substances until injected substances run out.

The liquid chemicals are contained in the container part of the cartridge, and the top opening of the container part is covered with the permeable membrane. Thus, vibration while driving causes no spill of the liquid chemicals, and the steam fog generator for vehicle is more suitable for use in vehicles than a conventional device that may cause a spill of liquid aromatic substances through an injection hole.

In the steam fog generator for vehicle according to claim 2, turning on and off the operating switch provided in the steam fog generator body allows the amount of transpired liquid chemicals to be adjusted.

For use in the vehicle of the type that always supplies power to the accessory socket regardless of the states of the key switch, turning off the operating switch when getting off the vehicle prevents the battery from being unnecessarily drained without the plug part being detached from the accessory socket.

In the steam fog generator for vehicle according to claim 3, the amount of liquid chemicals remaining in the cartridge held in the steam fog generator body can be visually checked. Thus, the replacement timing of the cartridge can be anticipated to provide for replacement of the cartridge.

In the steam fog generator for vehicle according to claim 4, the protruding direction into the cabin can be changed by folding the steam fog generator body extending from the plug part toward the plug part. This allows accommodation depending on usage patterns and improves convenience.

At this time, the folding direction of the steam fog generator body is limited by the limiting means to the bottom side of the held cartridge. Thus, folding of the top opening of the cartridge toward the front wall surface of the driver's seat can be prevented, and the permeable membrane of the container part through which the liquid chemicals in the cartridge pass can be directed into the cabin. This allows the transpired liquid chemicals to be diverged into the cabin.

The invention claimed is:

1. A steam fog generator for vehicle comprising:
a plug part attachable to and detachable from an accessory socket provided in a cabin;
a steam fog generator body extending from said plug part into the cabin, power being supplied from the vehicle through said plug part;
said steam fog generator body including a holding part for attachably and detachably holding a cartridge containing liquid chemicals, a heating element that produces heat by the power supplied through said plug part to heat said liquid chemicals in a container part of said cartridge and allows said liquid chemicals to pass outward through a permeable membrane covering a top opening of said container part, and divergence means for diverging said liquid chemicals having passed through said permeable membrane into the cabin;
said steam fog generator body including an operating switch for turning on and off the power to be supplied to said heating element;
said holding part including a loading/unloading port for loading and unloading said cartridge into and from said steam fog generator body, and a storage space for loadably and unloadably storing said cartridge inserted through said loading/unloading port;
said divergence means being constituted by a divergence port that provides communication between said storage space and the outside;
at least one of said container part and said permeable membrane of said cartridge, and said steam fog generator body being made of a transparent material;
said steam fog generator body including an observation part for observing the amount of liquid remaining in said cartridge; and
said steam fog generator body extending from said plug part being foldably connected to said plug part, and limiting means being provided for limiting a folding direction of said steam fog generator body to a bottom side of said held cartridge.

2. A steam fog generator for vehicle, comprising:
a plug part attachable to and detachable from an accessory socket provided in a cabin;
a steam fog generator body extending from said plug part into the cabin, power being supplied from the vehicle through said plug part,
said steam fog generator body including a holding part for attachably and detachably holding a cartridge containing liquid chemicals, a heating element that produces heat by the power supplied through said plug part to heat said liquid chemicals in a container part of said cartridge and allows said liquid chemicals to pass outward through a permeable membrane covering a top opening of said container part, and divergence means for diverging said liquid chemicals having passed through said permeable membrane into the cabin; and
said steam fog generator body extending from said plug part being foldably connected to said plug part, and limiting means being provided for limiting a folding direction of said steam fog generator body to a bottom side of said held cartridge.

3. The steam fog generator for vehicle according to claim 2, wherein said steam fog generator body includes an operating switch for turning on and off the power to be supplied to said heating element.

4. A steam fog generator for generating fog in a cabin of a vehicle which is provided with power from an accessory socket of the vehicle, the steam fog generator comprising:
a plug part plugable into and removable from the accessory socket and which provides a connection delivering power;
a generator body extending from said plug part into the cabin and into which the power is supplied from the accessory socket through said plug part, said generator body having a first end disposed at said plug part and a second end distal with respect to said first end;
a cartridge having first and second cartridge end portions and a body portion therebetween defining a cavity containing liquid chemicals and including an aperture in communication with said cavity, and said cartridge including a permeable membrane covering said aperture and permitting said liquid chemicals to pass through said permeable membrane;
said generator body including a holding portion for attachably and detachably receiving said cartridge, said generator body enclosing at least said first cartridge end portion and said body portion of said cartridge within the holding portion when said cartridge is at an installed position fully inserted in said holding portion;
said generator body having an exterior surface defining a loading aperture in communication with said holding portion, said loading aperture and said holding portion being configured such that loading and unloading of said cartridge is effected by sliding said cartridge with said first cartridge end portion forward through said loading aperture and into said installed position whereat said cartridge is fully inserted to a capacity of said holding portion of said generator body;

a heating element electrically connected to said plug part to receive the power supplied through said plug part, said plug part being disposed to heat said liquid chemicals in said cartridge promoting passage of said liquid chemicals through said permeable membrane;

said generator body being pivotably connected to said plug part so as to be positionable in a first position in an operational state wit said cartridge at said installed position, said generator body extending substantially in line with an axis of said plug part when in said first position, and said generator body being positionable to a second position in said operable stare wit said cartridge at said installed position wherein said generator body is at an angle to said axis of said plug part; and a communicating structure delivering said liquid chemicals, which passed through said permeable membrane, out from said generator body into the cabin.

5. The steam fog generator according to claim 4, wherein said generator body is configured such that said cartridge, when disposed at said installed position, has said second cartridge end portion exposed to outside said generator body via said loading aperture.

6. The steam fog generator according to claim 5, wherein said generator body is configured such that said cartridge, when disposed at said installed position, extends out from said generator body beyond at least a portion of said exterior of said generator body.

7. The steam fog generator according to claim 6, wherein:
said holding portion defines a storage cavity for said cartridge; and
said communicating structure includes said generator body having apertures in said exterior surface and in communication with said storage cavity for delivering said liquid chemicals passing through said permeable membrane to an area outside said generator body.

8. The steam fog generator according to claim 7, wherein:
at least one of a portion of said cartridge and said permeable membrane is made of a transparent material; and
said generator body includes an observation part for observing the amount of liquid remaining in said cartridge.

9. The steam fog generator according to claim 8, further comprising an operating switch for turning on and off the power supplied to said heating element.

10. The steam fog generator for generating fog in a cabin of a vehicle which is provided with power from an accessory socket of the vehicle, the steam fog generator comprising:
a plug part plugable into and removable from the accessory socket and which provides a connection delivering power;
a generator body extending from said plug part into the cabin and into which the power is supplied from the accessory socket through said plug part, said generator body having a first end disposed at said plug pan and a second end distal with respect to said first end;
a cartridge having first and second cartridge end portions and a body portion therebetween defining a cavity containing liquid chemicals and including an aperture in communication with said cavity, and said cartridge including a permeable membrane covering said aperture and permitting said liquid chemicals to pass through said permeable membrane;
said generator body including a holding portion for attachably and detachably receiving said cartridge, said generator body enclosing at least said first cartridge end portion and said body portion of said cartridge within the holding portion when said cartridge is at an installed position fully inserted in said holding portion;

said generator body having an exterior surface defining a loading aperture in communication with said holding portion, said loading aperture and said holding portion being configured such that loading and unloading of said cartridge is effected by sliding said cartridge with said first cartridge end portion forward through said loading aperture and into said installed position whereat said cartridge is fully inserted to a capacity of said holding portion of said generator body;

a heating element disposed fixed to said generator body at a position extending along a side wail of said holding portion in a direction of said sliding of said cartridge, said heating element being electrically connected to said plug part to receive the power supplied through said plug part, said plug part being disposed to heat said liquid chemicals in said cartridge promoting passage of said liquid chemicals through said permeable membrane; and a communicating structure delivering said liquid chemicals, which passed through said permeable membrane, out from said generator body into the cabin.

11. The steam fog generator of claim 10 wherein said cartridge comprises:
first and second opposing side walls opposing each other, third and fourth opposing side walls opposing each other, and a bottom wall adjoining said first, second, third and fourth opposing side walls;
said first, second, third and fourth opposing side walls in combination with said bottom wall defining said cavity; and
said permeable membrane extending in a plane defined by edges of said first, second, third and fourth opposing side walls.

12. The steam fog generator of claim 11 wherein said edges of said first, second, third and fourth opposing side walls define said aperture.

13. The steam fog generator of claim 12 wherein:
said first and second opposing side walls extend from said first cartridge end portion to said second cartridge end portion and said first and second opposing walls respectively have first and second flanges extending outward therefrom; and
said holding portion includes first and second guide surfaces configured to slidably engage said first and second flanges.

14. The steam fog generator of claim 13 wherein said heating element is disposed adjacent to said bottom wall so as to transfer heat through said bottom wall to said liquid chemicals.

15. The steam fog generator of claim 12 wherein said heating element is disposed adjacent to said bottom wall so as to transfer heat through said bottom wall to said liquid chemicals.

16. The steam fog generator of claim 11 wherein said heating element is disposed adjacent to said bottom wall so as to transfer heat through said bottom wall to said liquid chemicals.

17. The steam fog generator of claim 11 wherein:
said first and second opposing side walls extend from said first cartridge end portion to said second cartridge end portion and said first and second opposing walls respectively have first and second flanges extending outward therefrom; and said holding portion includes first and second guide surfaces configured to slidably engage said first and second flanges.

18. The steam fog generator of claim 17 wherein said heating element is disposed adjacent to said bottom wall so as to transfer heat through said bottom wall to said liquid chemicals.

19. The steam fog generator of claim 18 wherein said cartridge includes a planar member extending from said second end portion and protruding through said loading aperture, when said cartridge is in a fully installed position, to be exposed to outside of the steam fog generator.

20. The steam fog generator of claim 10 wherein said cartridge includes a planar member extending from said second end portion and protruding through said loading aperture, when said cartridge is in a fully installed position, to be exposed to outside of the steam fog generator.

* * * * *